United States Patent
Chuter et al.

(10) Patent No.: US 7,135,037 B1
(45) Date of Patent: Nov. 14, 2006

(54) SYSTEM AND METHOD FOR FORMING A JUNCTION BETWEEN ELEMENTS OF A MODULAR ENDOVASCULAR PROSTHESIS

(75) Inventors: Timothy A. M. Chuter, Burlingame, CA (US); David T. Pollock, Burlingame, CA (US); Tamara L. Trayer, Belmont, CA (US)

(73) Assignee: Endovascular Technologies, Inc., Santa Clara, CA (US)

( * ) Notice: Subject to any disclaimer, the term of this patent is extended or adjusted under 35 U.S.C. 154(b) by 0 days.

(21) Appl. No.: 09/562,295

(22) Filed: May 1, 2000

(51) Int. Cl.
*A61F 2/06* (2006.01)
*A61F 2/24* (2006.01)

(52) U.S. Cl. ................ 623/1.1; 606/108; 606/194; 606/195; 606/198

(58) Field of Classification Search ............ 606/108, 606/191, 192, 194, 195, 198; 623/1.1–1.36
See application file for complete search history.

(56) References Cited

U.S. PATENT DOCUMENTS

| | | | |
|---|---|---|---|
| 5,064,435 A | 11/1991 | Porter | |
| 5,522,881 A | 6/1996 | Lentz | |
| 5,562,724 A | 10/1996 | Vorwerk et al. | |
| 5,575,817 A | 11/1996 | Martin | |
| 5,632,772 A | 5/1997 | Alcime et al. | |
| 5,639,278 A | 6/1997 | Dereume et al. | |
| 5,653,743 A | 8/1997 | Martin | |
| 5,676,696 A | 10/1997 | Marcade | |
| 5,683,449 A | 11/1997 | Marcade | |
| 5,683,450 A | 11/1997 | Goicoechea et al. | |
| 5,713,917 A | 2/1998 | Leonhardt et al. | |
| 5,716,365 A | 2/1998 | Goicoechea et al. | |
| 5,718,724 A | 2/1998 | Goicoechea et al. | |
| 5,755,770 A | 5/1998 | Ravenscroft | |
| 5,755,772 A | 5/1998 | Evans et al. | |
| 5,755,773 A | 5/1998 | Evans et al. | |
| 5,776,180 A | 7/1998 | Goicoechea et al. | |
| 5,800,508 A | 9/1998 | Goicoechea et al. | |
| 5,824,037 A | 10/1998 | Fogarty et al. | |
| 5,824,042 A | 10/1998 | Lombardi et al. | |
| 5,827,310 A | 10/1998 | Marin et al. | |
| 5,843,160 A | 12/1998 | Rhodes | |
| 5,855,598 A | 1/1999 | Pinchuk | |

(Continued)

FOREIGN PATENT DOCUMENTS

FR    2 748 197 A1    11/1997

*Primary Examiner*—Vy Q. Bui
(74) *Attorney, Agent, or Firm*—Fulwider Patton LLP

(57) ABSTRACT

The present invention provides a system and a method for forming in vivo a junction between a first and a second element of a modular endovascular prosthesis used for repairing defects in vessels and other lumens within the body of a patient. The first element is adapted to have a receiving element, and the second element is adapted to have a protruding element. In the final deployed configuration of the endovascular prosthesis, the protruding element of the second element is adapted to be engaged with the receiving element of the first element, substantially preventing axial separation of the elements relative to each other. The receiving element of the invention may have various forms, and may include a fold in the wall of the first element, an expandable framework having protruding struts, or a flexible thread. The protruding elements of the invention may be formed from an expandable framework having protruding struts, or may be formed from a fold in the wall of the second element, or may comprise a flexible thread.

13 Claims, 18 Drawing Sheets

U.S. PATENT DOCUMENTS

| | | |
|---|---|---|
| 5,860,998 A | 1/1999 | Robinson et al. |
| 5,916,263 A | 6/1999 | Goicoechea et al. |
| 5,938,696 A | 8/1999 | Goicoechea et al. |
| 5,993,481 A | 11/1999 | Marcade et al. |
| 6,015,431 A | 1/2000 | Thornton et al. |
| 6,016,810 A | 1/2000 | Ravenscroft |
| 6,051,020 A | 4/2000 | Goicoechea et al. |
| 6,099,558 A | 8/2000 | White et al. |
| 6,102,938 A | 8/2000 | Evans et al. |
| 6,117,167 A | 9/2000 | Goicoechea et al. |
| 6,123,722 A | 9/2000 | Fogarty et al. |
| 6,149,682 A | 11/2000 | Frid |
| 6,695,875 B1 | 2/2004 | Stelter et al. |

SYSTEM AND METHOD FOR FORMING A JUNCTION BETWEEN ELEMENTS OF A MODULAR ENDOVASCULAR PROSTHESIS

BACKGROUND OF THE INVENTION

The present invention relates generally to intraluminal endovascular prostheses which are used for repairing defects in vessels and other lumens within the body of a patient. More particularly, the present invention relates to systems and methods for forming, in vivo, a robust junction between one element of a modular endovascular prosthesis which has been implanted in a patient, and another element.

Aneurysms are discrete dilations of the arterial wall. One of the most common, and among the most life threatening, is an aneurysm of the abdominal aorta between the renal and iliac arteries. If untreated, the aneurysm dilates progressively with an ever increasing risk of rupture and hemorrhagic death.

One method of treatment is provided by direct surgical intervention, in which the defective vessel may be bypassed or replaced using a prosthetic device such as a synthetic graft. The risks involved in direct surgical intervention of this magnitude are great, and include an extensive recovery period and a high morbidity rate.

In recent years a less invasive method of treatment has evolved through a series of inventions. The details vary, but, conventionally, a resilient tubular conduit fashioned from flexible material (herein referred to as a "graft") is introduced into the defective vessel by means of catheters introduced into the femoral artery. The graft may be attached to the non-dilated arteries above and below the aneurysm using expanding metallic or plastic cylinders which may include barbs or hooks. The fluid pressure on the diseased arterial wall is reduced by the barrier provided by the graft. The field of art has developed since its early stages and in certain circumstances the implantation of grafts in the patient in "modular" form is now possible and may be desirable. A modular graft is one made up of different modular elements, each of which is implanted in the patient at a different stage, the different elements then being joined to each other by a suitable junction in vivo—that is, after introduction into the patient's vascular system.

While modular grafts have the advantage of reducing problems such as twisting of the graft during deployment, their use and the necessary formation in vivo of a junction between their elements is nevertheless attended by numerous complications. The most troubling long-term complication specific to the junction includes disruption of the junction, which may be caused by dislocation of one element relative to another through vascular movement or may be the long-term consequence of downstream fluid force. Once a junction between modular elements of an endovascular prosthesis has been disrupted, fluid leakage into the region between the prosthesis and vascular wall will likely follow, thereby diminishing the efficacy of the prosthesis in reducing fluid pressure on the diseased vascular wall.

In the prior art, there are various kinds of junction formed in vivo between tubular elements of a modular prosthesis. Conventionally, the junctions used in the art may depend upon friction between the overlapping elements to hold the elements in place relative to each other. In other cases, the overlapping portion of one element may be adapted to form a frustoconical shape compatible with the overlapping portion of the other element. This serves to enhance the frictional connection between the elements and provides a degree of mechanical connection. However, each of these junctions may be disrupted by a relatively small force.

In the prior art of endovascular repair with a modular prosthesis, there therefore exists a need to form in vivo a robust and secure junction between modular elements which will not be dislocated by vascular movement or downstream fluid flow. The present invention addresses needs which are found in the prior art.

SUMMARY OF THE INVENTION

Briefly, and in general terms, the present invention provides a system and a method for forming in vivo a junction between a first element and a second element of a modular endovascular prosthesis used for repairing defects in vessels and other lumens within the body of a patient.

According to the present invention, the first element of such modular prosthesis is adapted to include a protrusion receiving element, and the second element is adapted to include at least one protruding element. In the final deployed configuration, the protruding element is adapted to engage the receiving element to thereby provide a robust and secure junction.

In a preferred embodiment, the receiving element may be defined by thread loops circumferentially configured about an interior wall of the first element and adapted to receive the protruding element of the second element. In a further embodiment, the receiving element may be formed from an inward fold in the inner surface of the distal end of the first element to thereby define an annular pocket for receiving the second element. In yet further embodiments, the receiving element may embody an expandable framework having struts.

In a preferred embodiment, the second element is adapted to include at least one protruding element such as the strut of a frame which is adapted to engage the receiving element of the first element. In further embodiments, the protruding element may be formed from an outward fold in the wall of the second prosthetic element to define an annular pocket, or formed from thread loops attached to a wall of the second element.

In a preferred method of deploying first and second elements, the first element is deployed at a desired position within the patient's vasculature. Thereafter, the second element is positioned, in compressed condition, such that the protruding element of the second element is longitudinally clear of the receiving element. The second element is then expanded, allowing the protruding element to engage the first element. The interaction of the protruding element with the receiving element provides a barrier to axial separation of the two elements relative to each other.

It will be appreciated that, after implantation, longitudinal movement of the second element relative to the first element generally does not occur where the junction between the first and second prosthetic elements is arranged to benefit from forces associated with downstream fluid flow. Moreover, any force promoting longitudinal movement of the second element will be resisted by the frictional connection between the first and second elements.

Other features and advantages of the present invention will become apparent from the following detailed description, taken in conjunction with the accompanying drawings, which illustrate, by way of example, the principles of the invention.

DETAILED DESCRIPTION OF THE PREFERRED EMBODIMENTS

In general, the system and method of the present invention for forming a junction between first and second elements of a modular endovascular prosthesis is achieved by adapting the first element to include a receiving element, and by adapting the second element to include at least one protruding element which is configured to engage the receiving element and, thus, prevent axial separation of the first and second elements relative to each other.

Figure 1:
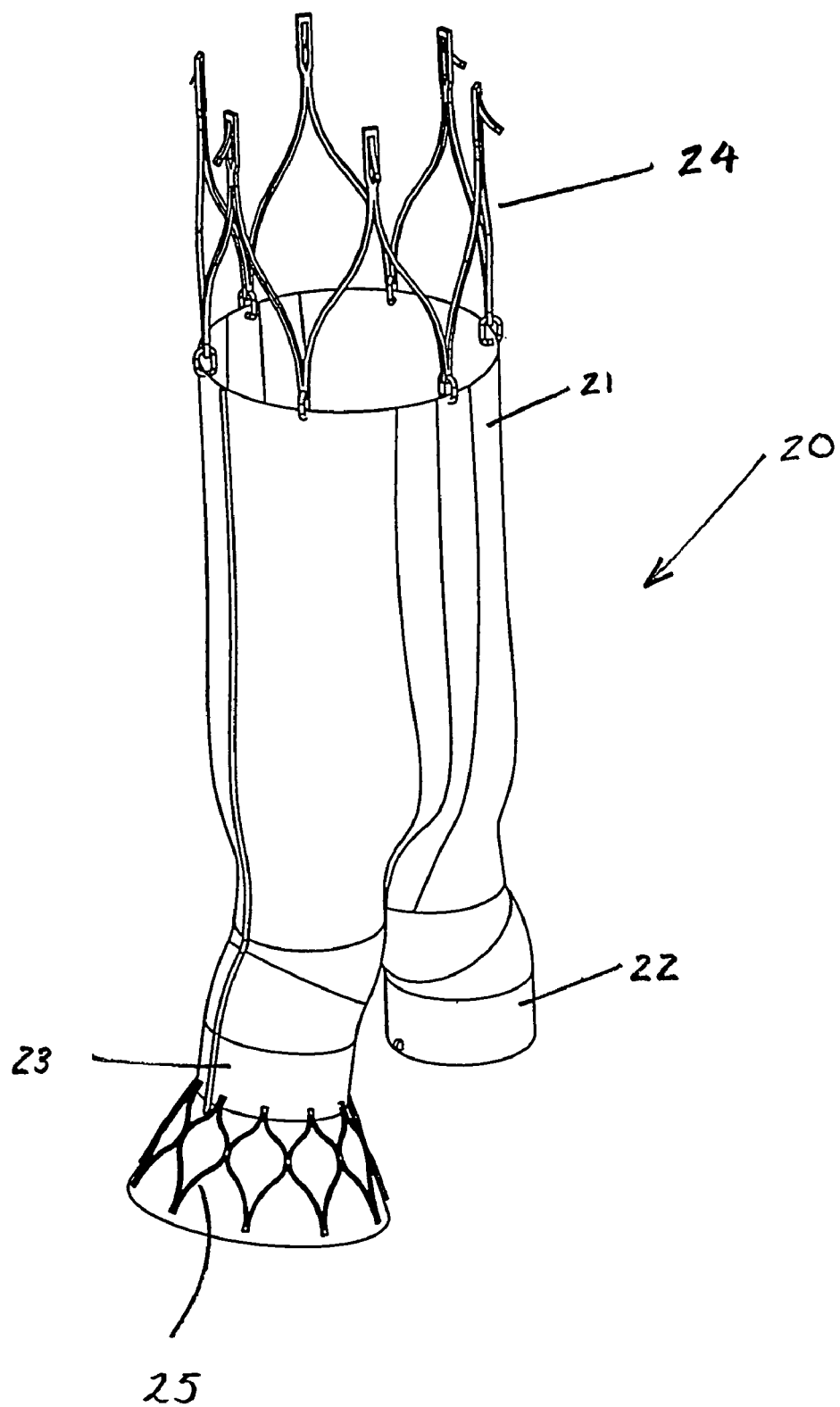
FIG. 1 is a perspective view, depicting a first component of a modular endovascular prosthesis.
Figure 2:
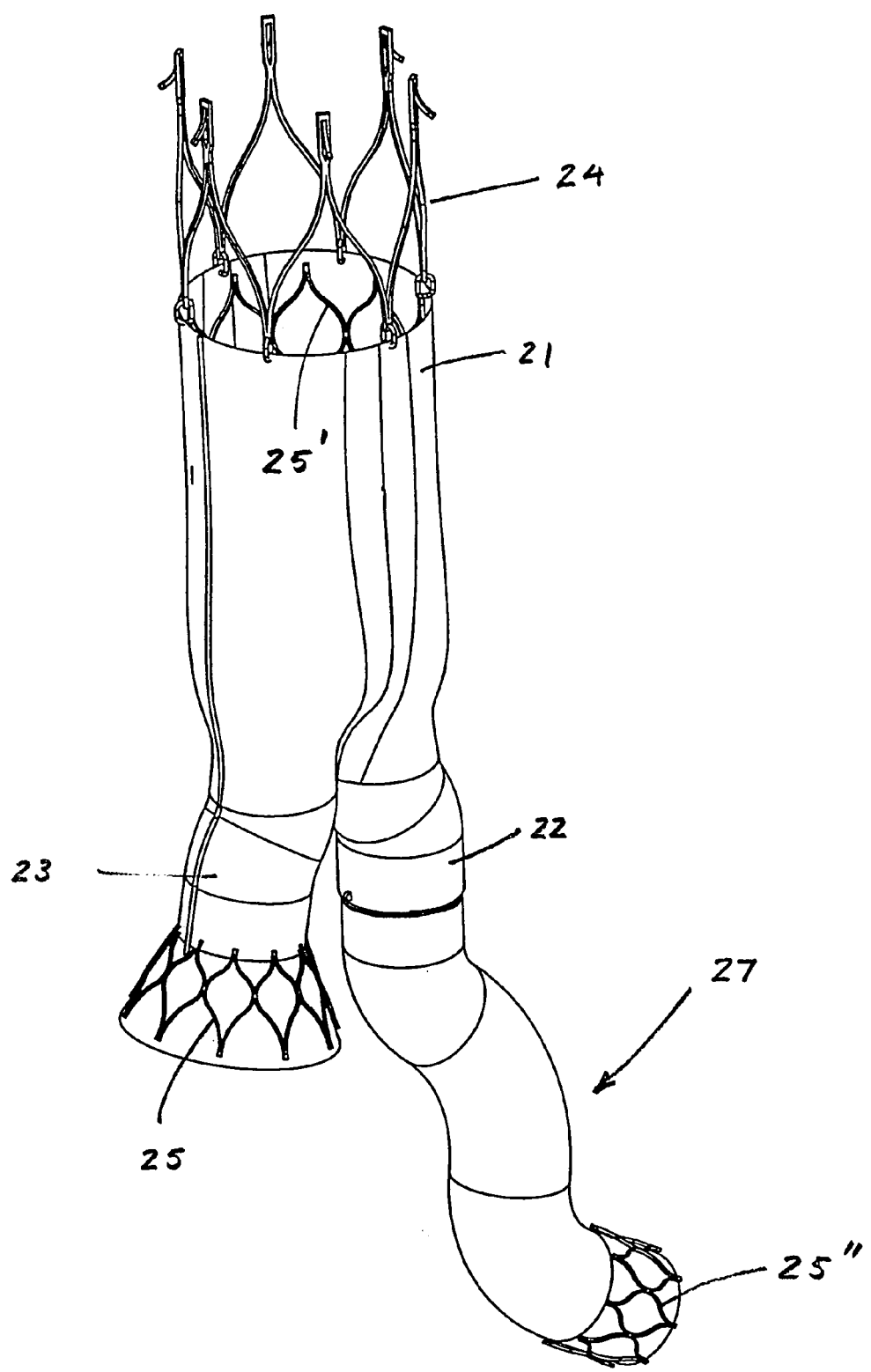
FIG. 2 is a perspective view, depicting a second component attached to the leg of the modular endovascular prosthesis shown in FIG. 1.
Figure 3:
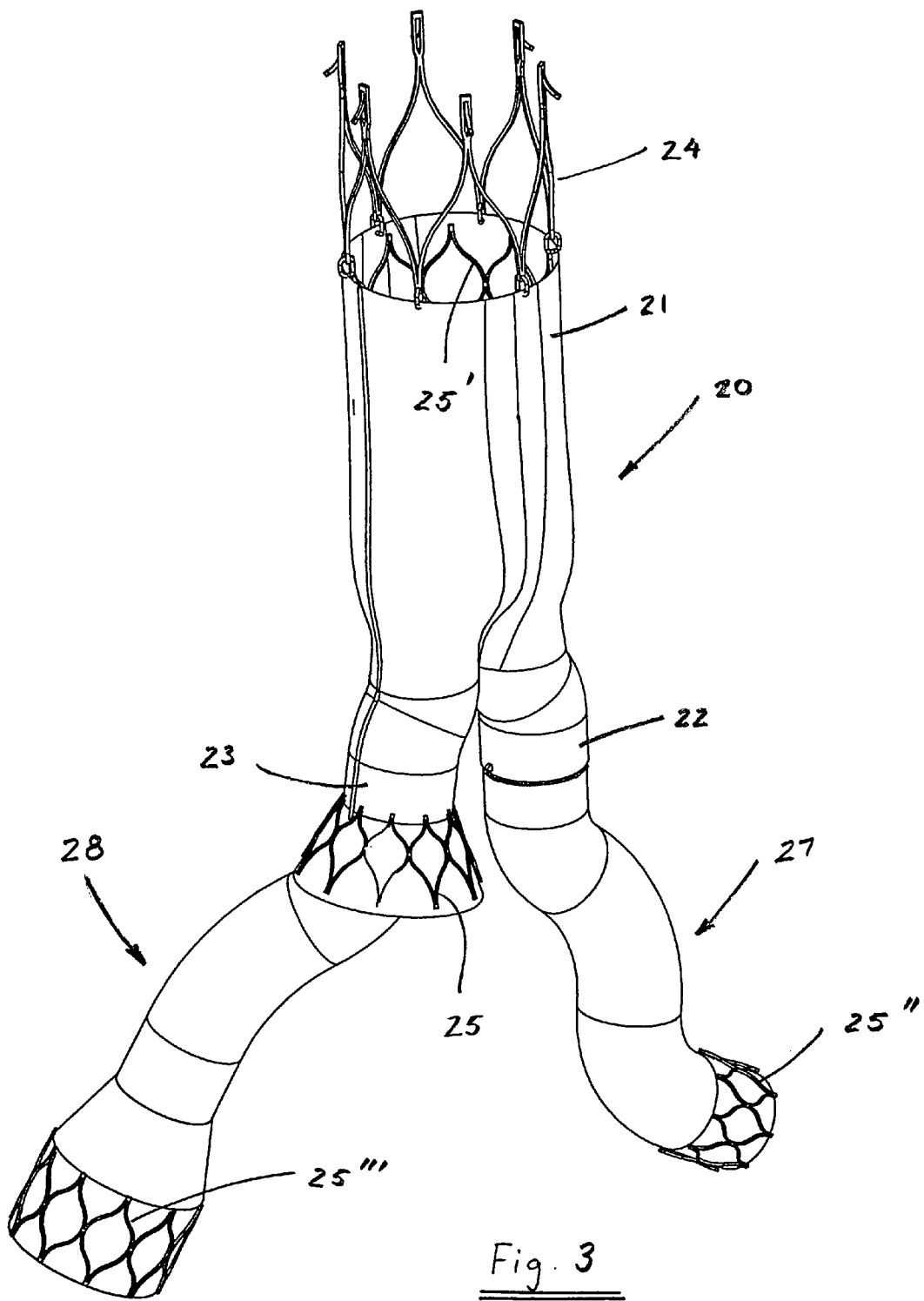
FIG. 3 is a schematic view, depicting a third component attached to the modular endovascular prosthesis shown in FIGS. 1 and 2.

Referring to FIGS. 1–3, an exemplary modular endovascular prosthesis incorporating the present invention is described. It will be appreciated by one of ordinary skill in the art that it is within the scope of the present invention to utilize the present junction at the joining of any two elements in other modular endovascular prosthesis as well for example the prostheses described in U.S. Pat. No. 5,993,481 to Marcade et al., U.S. Pat. No. 5,938,696 to Goicoechea et al., U.S. Pat. No. 5,713,917 to Leonhardt et al., U.S. Pat. No. 5,575,817 to Martin, U.S. Pat. No. 5,824,040 to Con et al., U.S. Pat. No. 5,824,037 to Fogarty et al., U.S. Pat. No. 5,632,772 to Alcime et al. and published Patent Cooperation Treaty WO 99/11199 to Kujawski et al. FIG. 1 shows a first component 20 of an endovascular prosthesis, configured to be used in the repair of a bifurcated corporeal vessel. The first component 20 has a trunk portion 21 and a pair of legs 22, 23. An expandable fixation device 24 may be connected to a superior end of the trunk 21 to facilitate attachment of the first component to a vascular wall of a target vessel. An expandable framework 25 may be used to maintain the patency of a lumen of the prosthesis where necessary.

FIG. 2 depicts a manner in which a second prosthetic component 27 may be connected to the inferior end of a leg 22 of the first component 20. FIG. 3 further exemplifies how a third prosthetic component 28 may be connected to the inferior end of the other leg 23 of the first component 20, which may be configured with a bell-bottom profile to assist the surgeon in introducing a third component 28 into the lumen of that leg 23. Further expandable frameworks 25', 25", 25''' are shown maintaining the patency of the lumens of the prosthesis, and may be attached to either the internal or external wall of the prosthesis, as shown. Additionally, further tubular components (not shown) may be added to exposed ends of the second and third components 27, 28, until the desired overall configuration is achieved, allowing fluid to flow from the first component 20 to the second 27 and third 28 components.

In modular systems such as the one shown in FIGS. 1–3, it is important to ensure that there is no leaking at junctions between the various components of the modular systems. One manner of providing such a junction is to configure one component at a junction with a receiving element and the other with a protruding element that is sealingly received in the receiving element.

Figure 4:
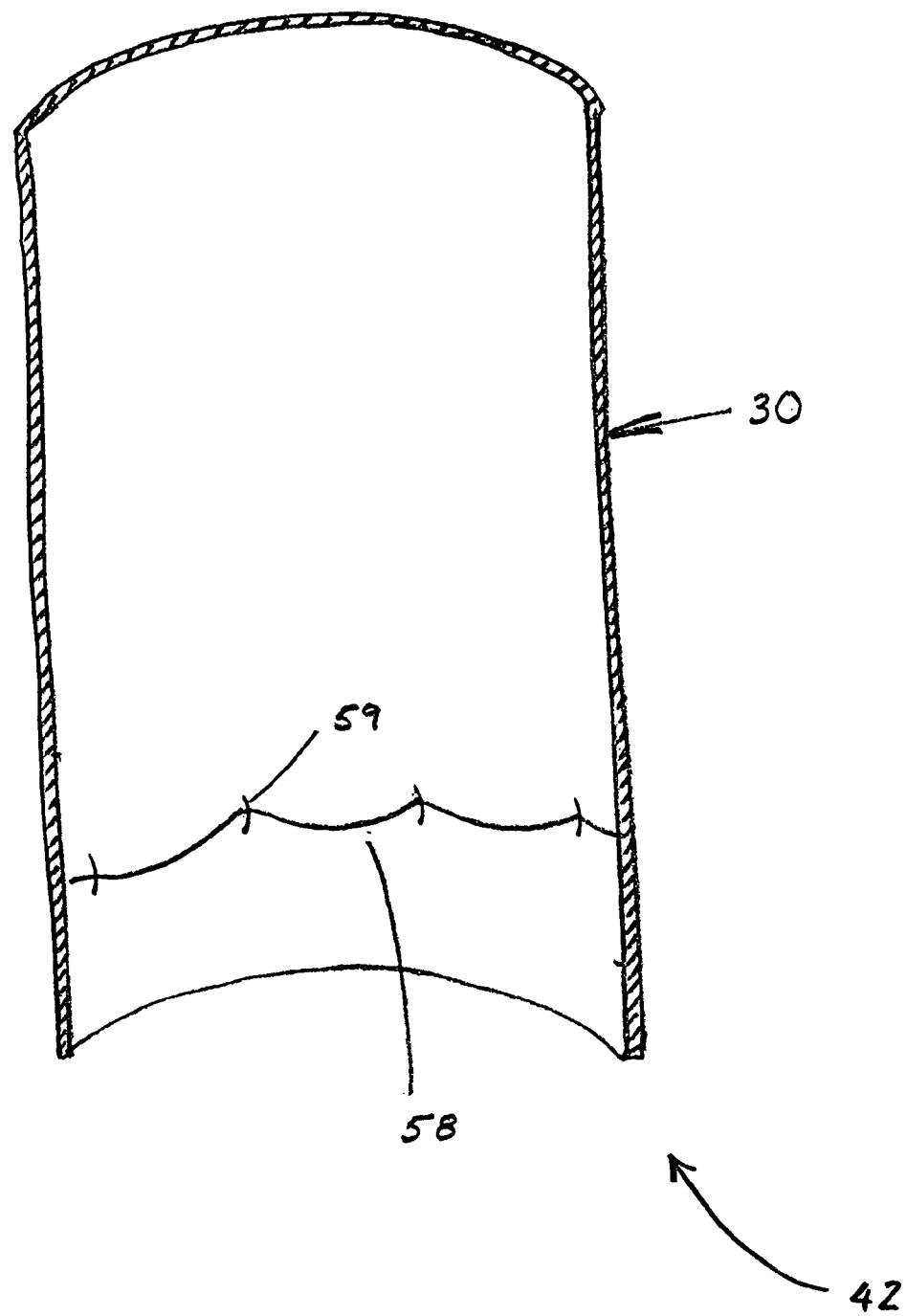
FIG. 4 is a cross-sectional view, depicting a first preferred embodiment of a receiving element.
Figure 5:
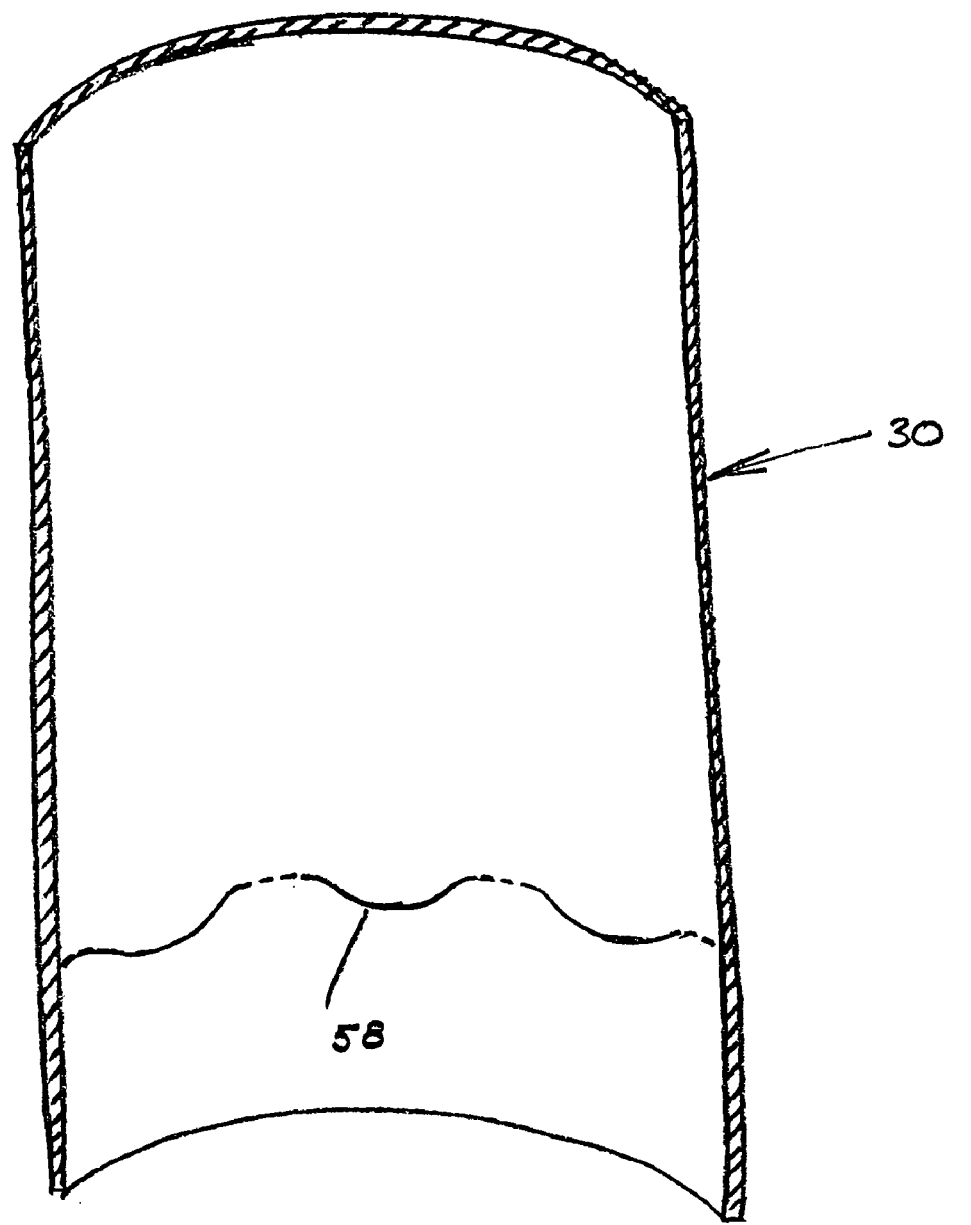
FIG. 5 is a cross-sectional view, depicting a variation of the receiving element of FIG. 4.

The receiving element of the present invention may assume a number of different forms. One aspect of the receiving element of the present invention is exemplified in FIG. 4, which shows a portion of a first prosthetic element 30 of a modular endovascular prosthesis, having an inferior end portion 42. A flexible thread 58 is circumferentially attached to the wall of the first prosthetic element 30 by means of connectors 59. The thread 58 is configured to have portions which suspend freely from the connectors 59, the same being adapted to receive and to retain a protruding element attached to a second prosthetic element, as will be more fully described herein. The connectors 59 may be simply stitched through the wall of the first prosthetic element 30. Both the thread 58 and the connectors 59 may be made from any flexible substance which is durable and biocompatible. For example, Dacron™ polyester suture material has been found to be suitable for forming the thread. In an alternative embodiment, the thread 58 may be routed in and out of the wall of the first prosthetic element 30, as exemplified in FIG. 5.

In a second embodiment of the receiving element of the present invention (FIG. 6), the inferior end-portion 42 of the first element 30 of the modular endovascular prosthesis, includes an annular pocket 44 formed by folding the first element inwards. The resultant annular pocket 44 includes a rim 45 and is secured in a fixed position by a plurality of ties 46, which may consist of threads, staples, stitches, rivets, wire, heat welding, or any suitable tying means. The assembly is thereby adapted to receive a protruding element connected to a second prosthetic element.

Figure 7:
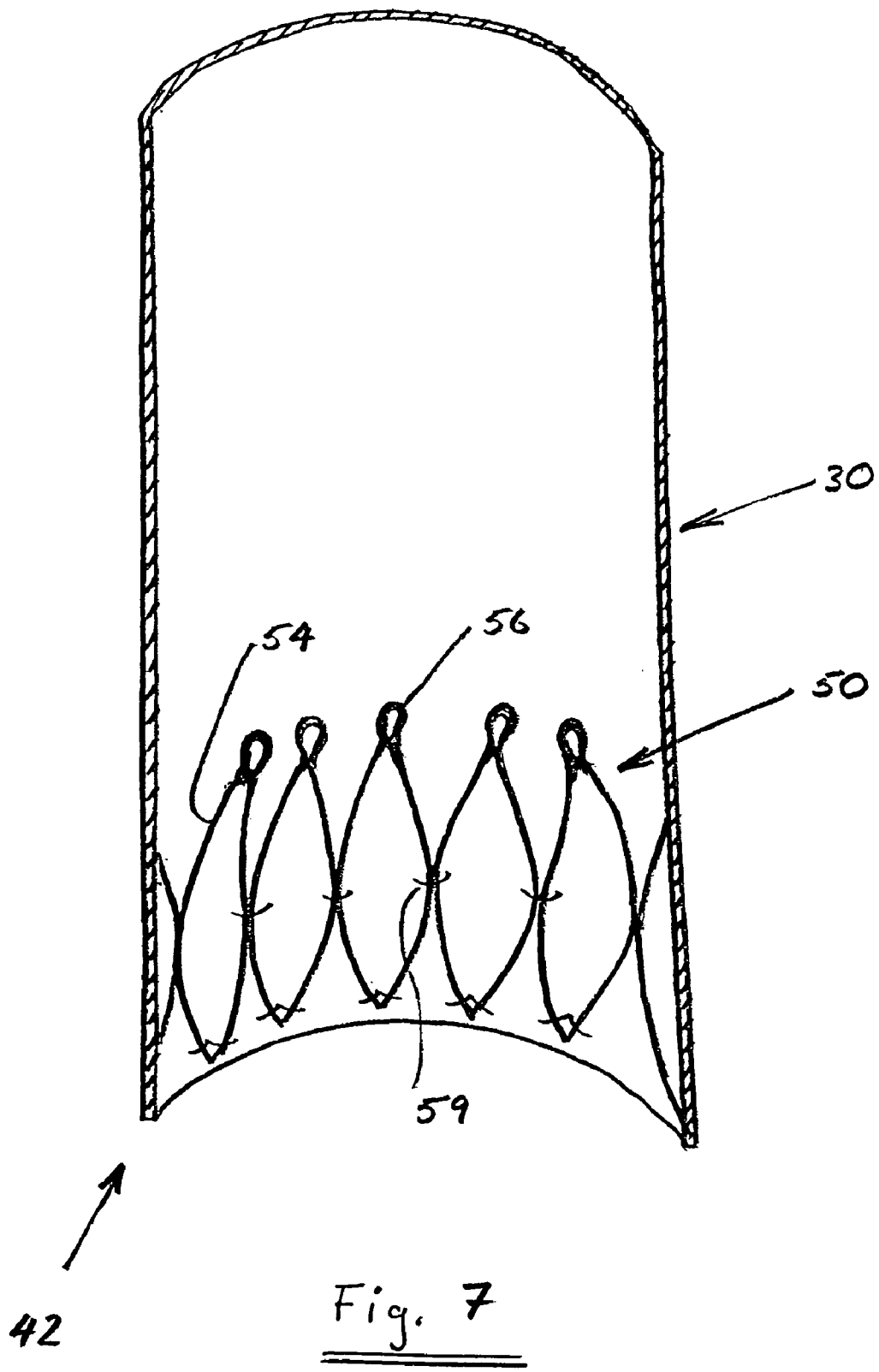
FIG. 7 is a cross-sectional view, depicting a third embodiment of a receiving element.

In a third embodiment (FIG. 7), the first prosthetic element 30 includes an expandable framework 50 attached to an interior wall of the first prosthetic element 30 by means of connectors 59. As with the previous embodiment, such connectors can consist of threads, staples, stitches, rivets, wire, heat welding, or any suitable tying means. The framework 50 has struts 54 which include tips 56 which are configured to protrude radially inward, thus providing an annular space suitable for receiving a protruding element attached to a second prosthetic element. The tips 56 of the struts 54 may be rounded, to prevent injury to any material of the prosthesis with which they might come into contact.

Figure 8:
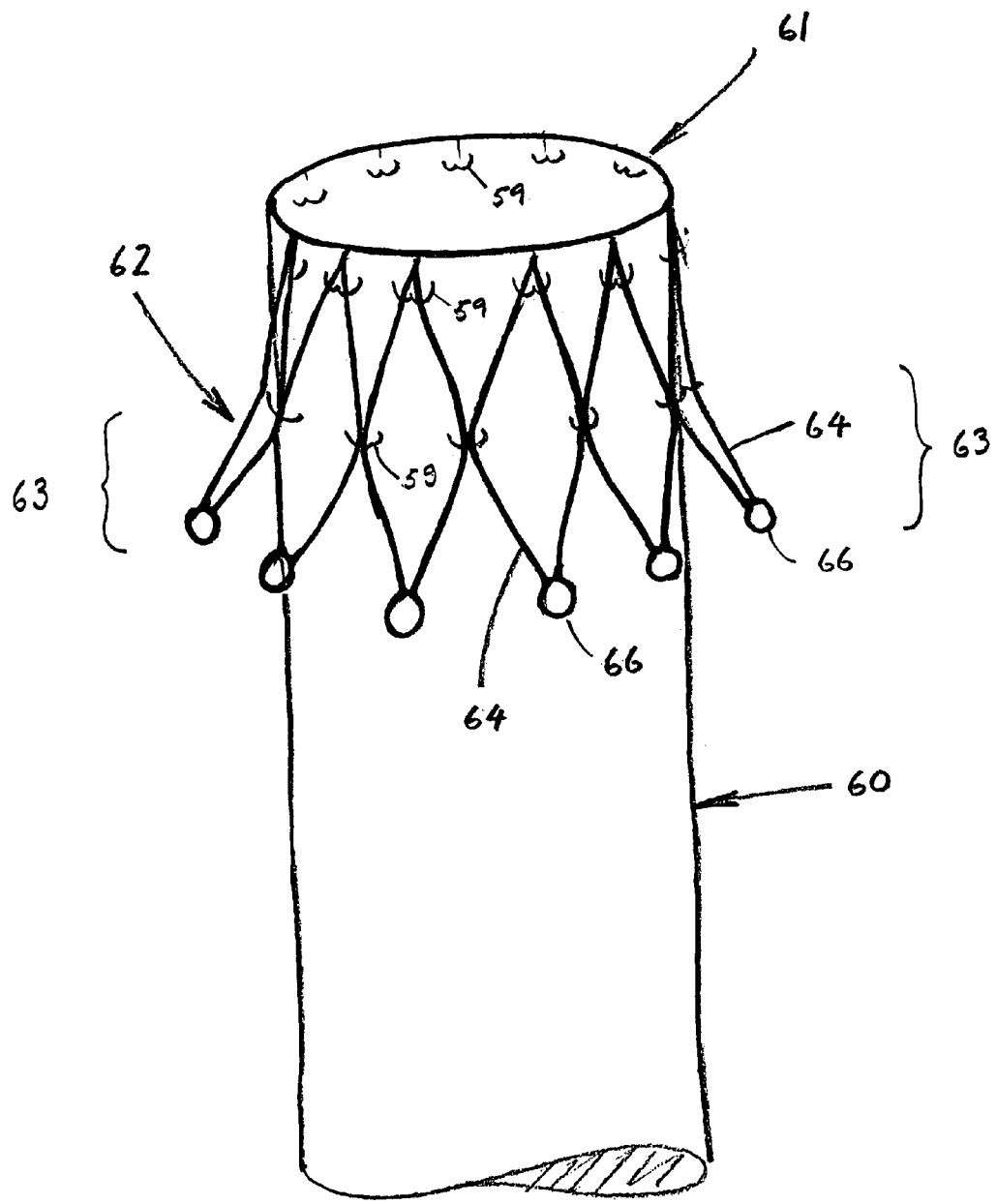
FIG. 8 is a perspective view, depicting a first embodiment of a protruding element.

The second prosthesis element of the present invention can assume a number of different forms. Turning to FIG. 8, there is shown one embodiment of a protruding element which is connected to a superior end-portion 61 of a second prosthetic element 60 which is configured to be joined to a first prosthetic element with a receiving element, such as those shown in FIGS. 4–7. The protruding element 61 may be formed by connecting an expandable framework 62 to the second prosthetic element 60. The expandable framework 62 includes a plurality of struts 64 which protrude radially outwardly. In a preferred embodiment, the framework 62 is attached to an outer wall of the second prosthetic element 60 by a plurality of connectors 59, which are of similar form and substance to the connectors previously described. The tips 66 of the protruding struts 64 may be rounded, so as to minimize any trauma to any prosthesis material with which they come into contact. The protruding element 61 of this embodiment is formed by the outwardly protruding struts 64 of the framework 62, which are adapted to be seated within a receiving element attached to a first prosthetic element.

Figure 9:
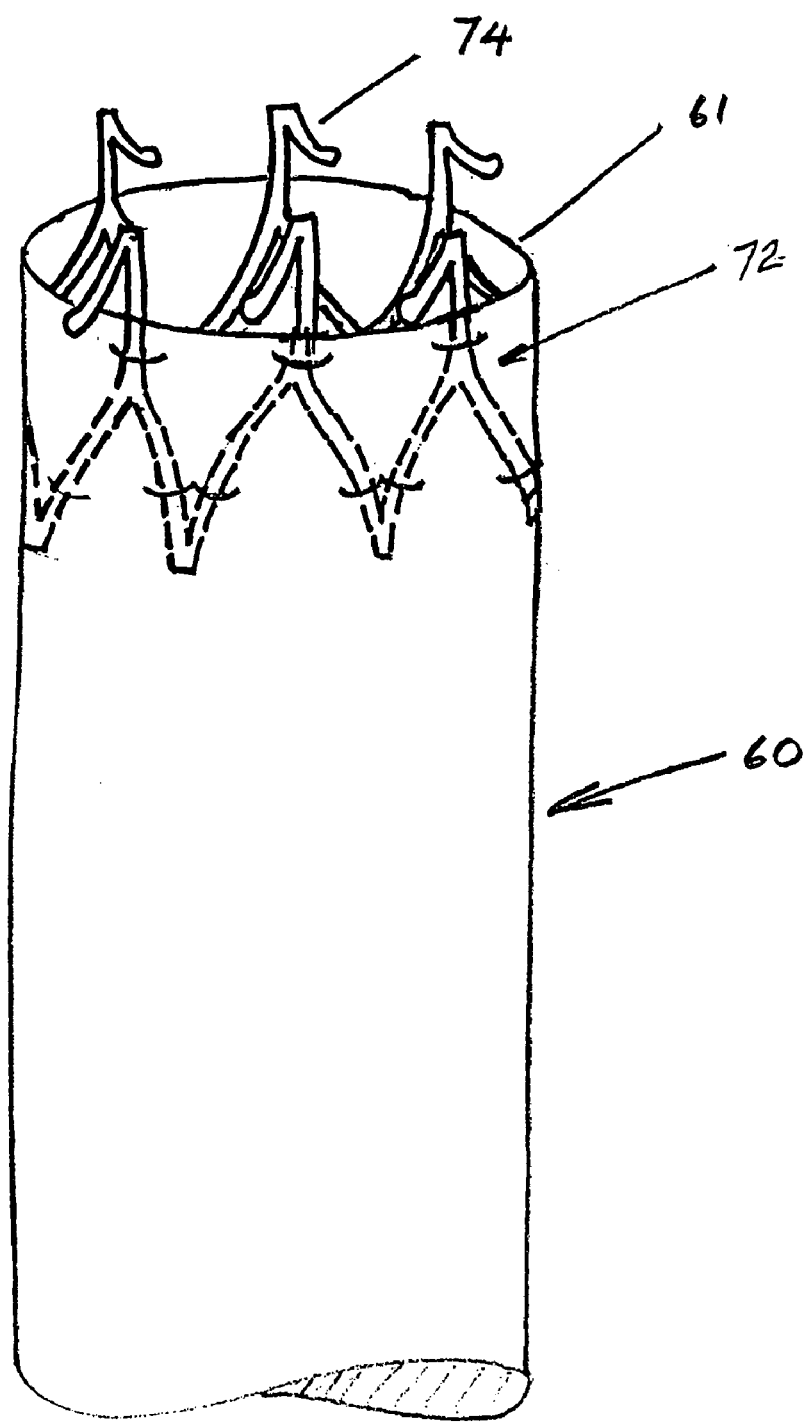
FIG. 9 is a perspective view, depicting a second embodiment of a protruding element.

FIG. 9 depicts a second embodiment of a protruding element of the present invention. In this aspect, the protruding element is defined by an expandable framework 72 having outwardly protruding struts 74 with blunt tips. The expandable framework 72 is adapted to be attached to inside walls of the second prosthetic element 60, allowing the struts to protrude radially outward beyond the superior end 61 of the second prosthetic element 60. The struts 72 may take a variety of forms, and may have a simple curved hook shape.

It will be appreciated that the expandable framework 62, 72 and the struts 64, 74 may have any shape which achieves the function of providing a protruding element suitable for engaging the receiving element of a first prosthetic element 30. In a preferred aspect of the invention, the framework 62, 72 may be self-expanding. However, in alternative embodiments a balloon-expanded framework may be used. The framework 62, 72 may be formed of a corrosion resistant material which has good spring and fatigue characteristics. Materials found to be particularly satisfactory are nickel-titanium alloys such as Nitinol, and chromium-cobalt-nickel alloys such as Elgiloy™.

Figure 10:
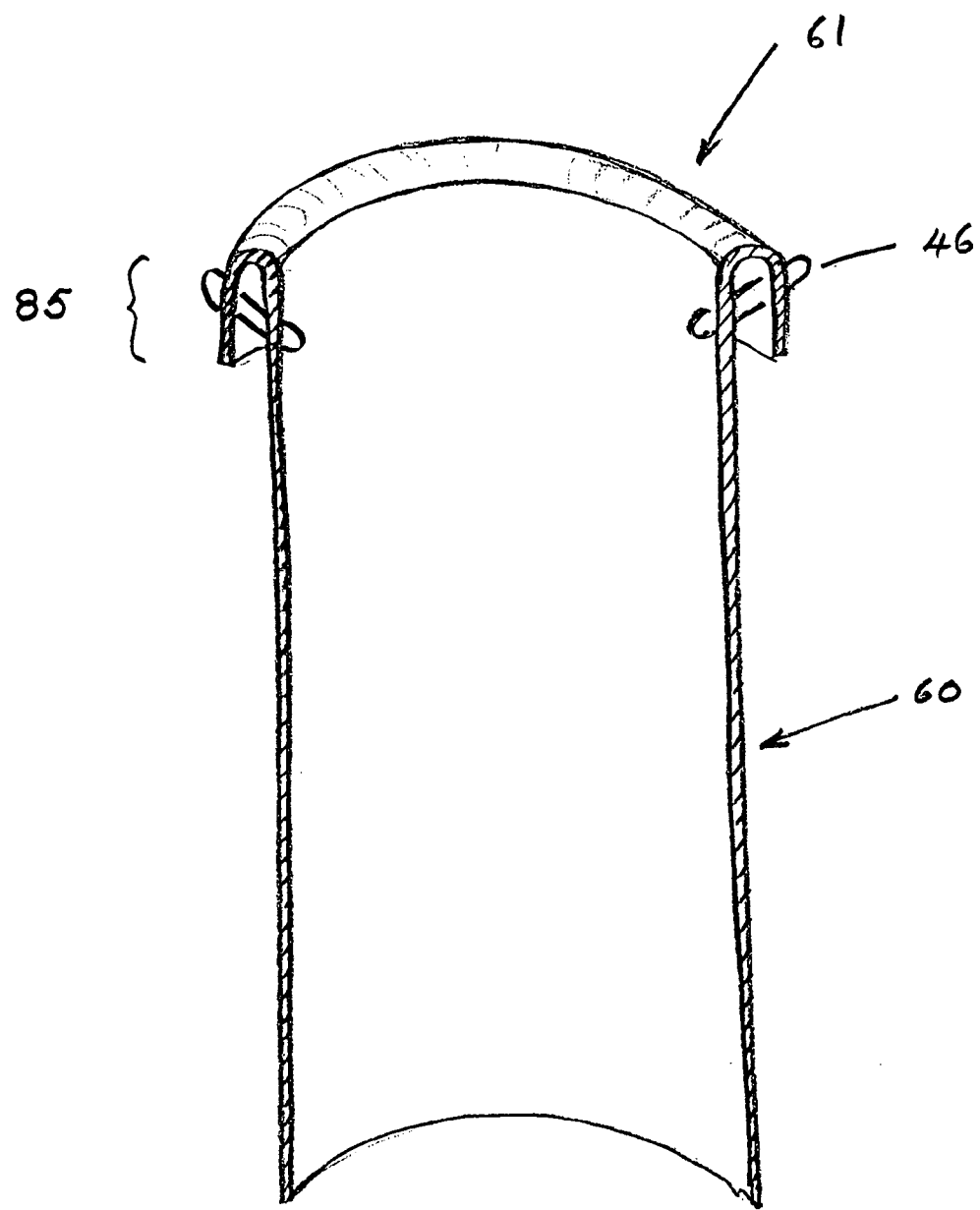
FIG. 10 is a cross-sectional view, depicting a third embodiment of the protruding element.
Figure 11:
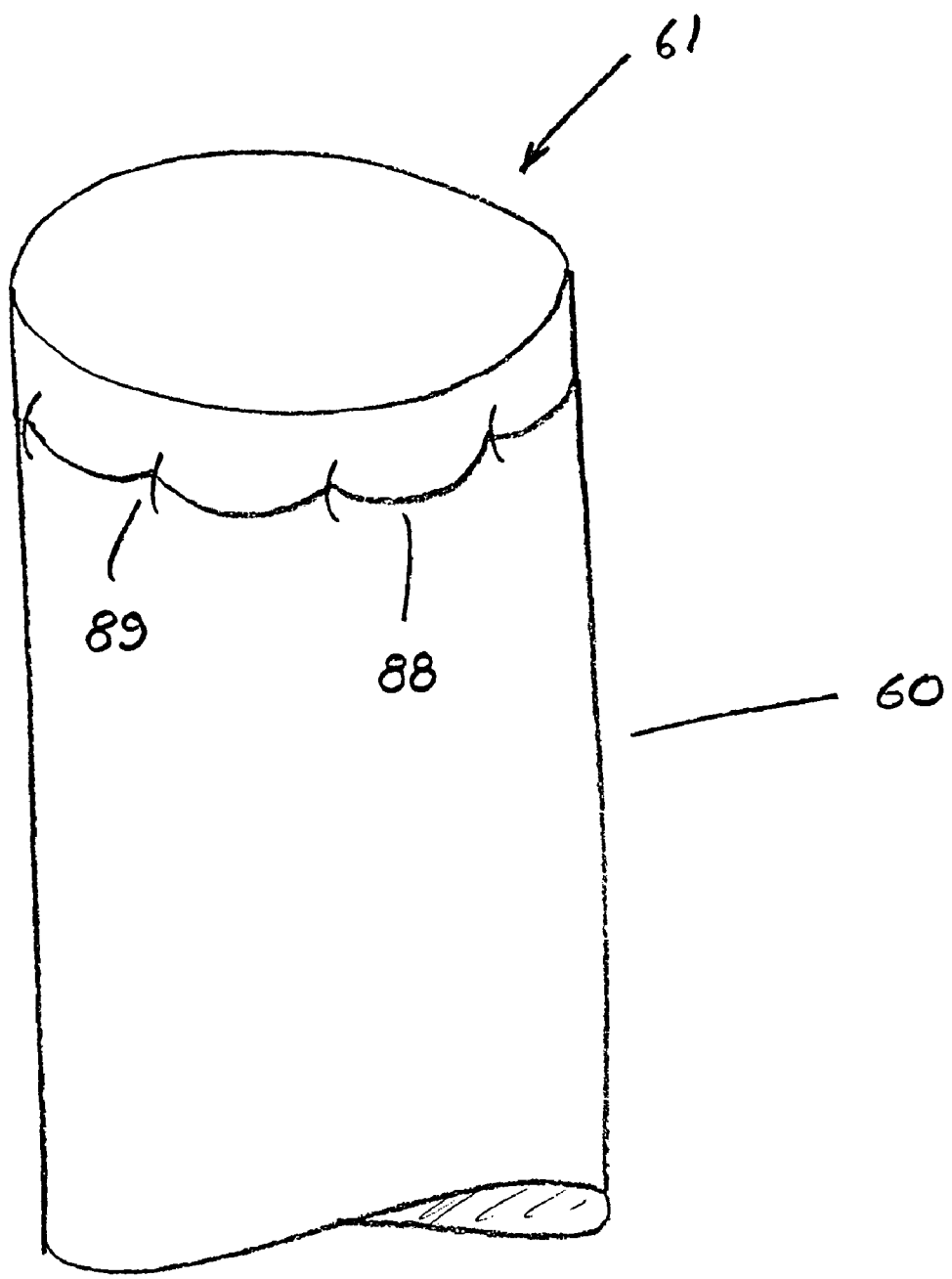
FIG. 11 is a perspective view, depicting a fourth embodiment of the protruding element.
Figure 12:
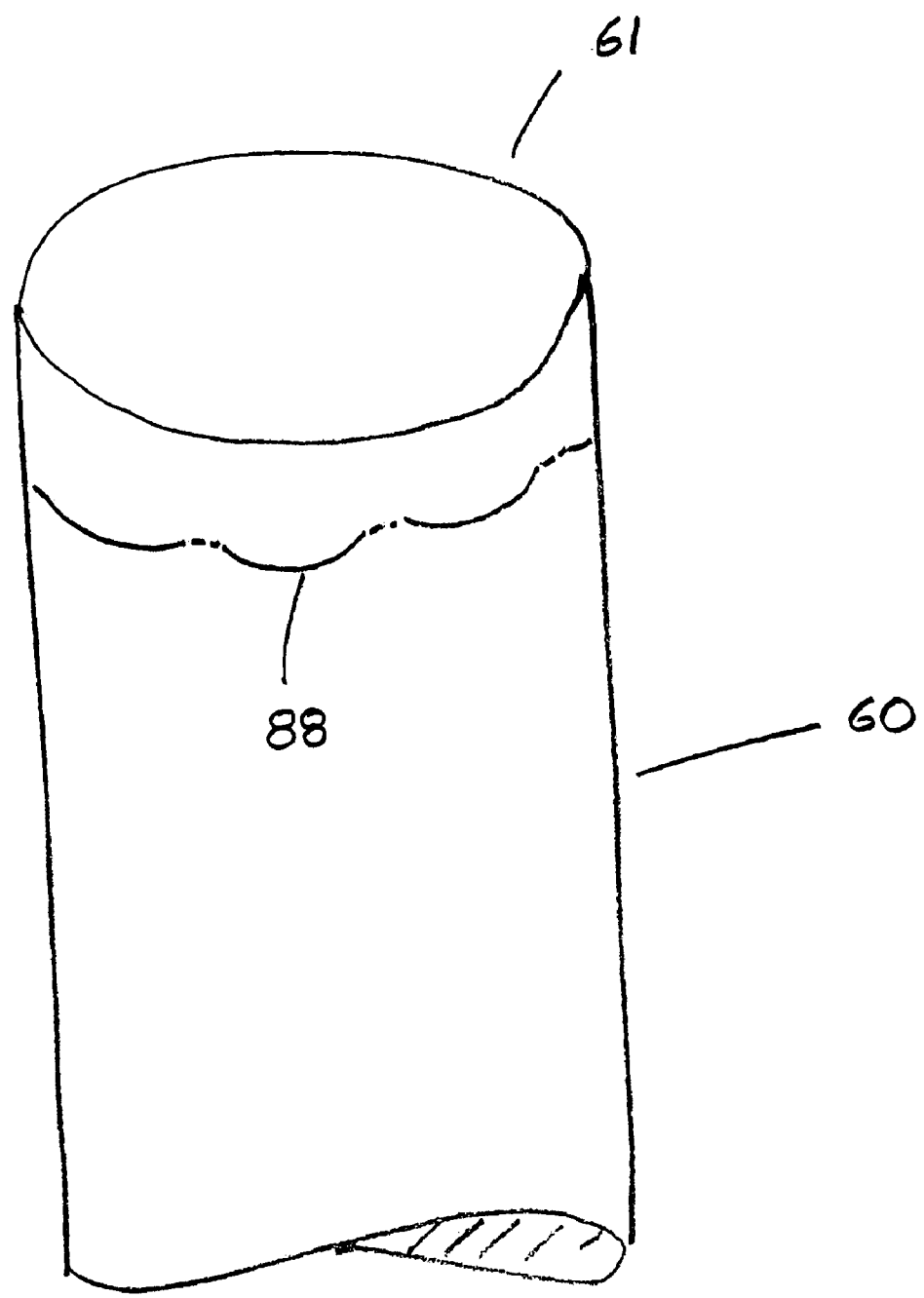
FIG. 12 is a perspective view, depicting a fifth embodiment of the protruding element.

With reference to FIG. 10, a third embodiment of the protruding element of the present invention is described for connecting with a receiving element as described. In this embodiment, the wall of the second prosthetic element 60 is folded radially outwardly, to form an external annular pocket 85. The folded pocket 85 may be secured in a fixed position in relation to the second prosthetic element by means of ties or connectors 46, such as have been previously described herein. Additionally, as shown in FIG. 11, the protruding element may be formed from a thread 88, circumferentially attached to the outer wall of the second prosthetic element 60. Attachment of the thread to this second element 60 may be achieved by connectors 89, or otherwise by routing the thread 88 in and out of the wall of the second prosthetic element, as exemplified in FIG. 12. It will be appreciated that, where the protruding element exemplified in FIGS. 10–12 is employed, the inferior end portion 61 of the second prosthetic element 60 may be expanded from a compressed condition to an expanded condition by using an expandable framework (not shown) similar to the expandable framework 62 described above, the same being placed on an interior wall of the second prosthetic element 60.

Figure 13:
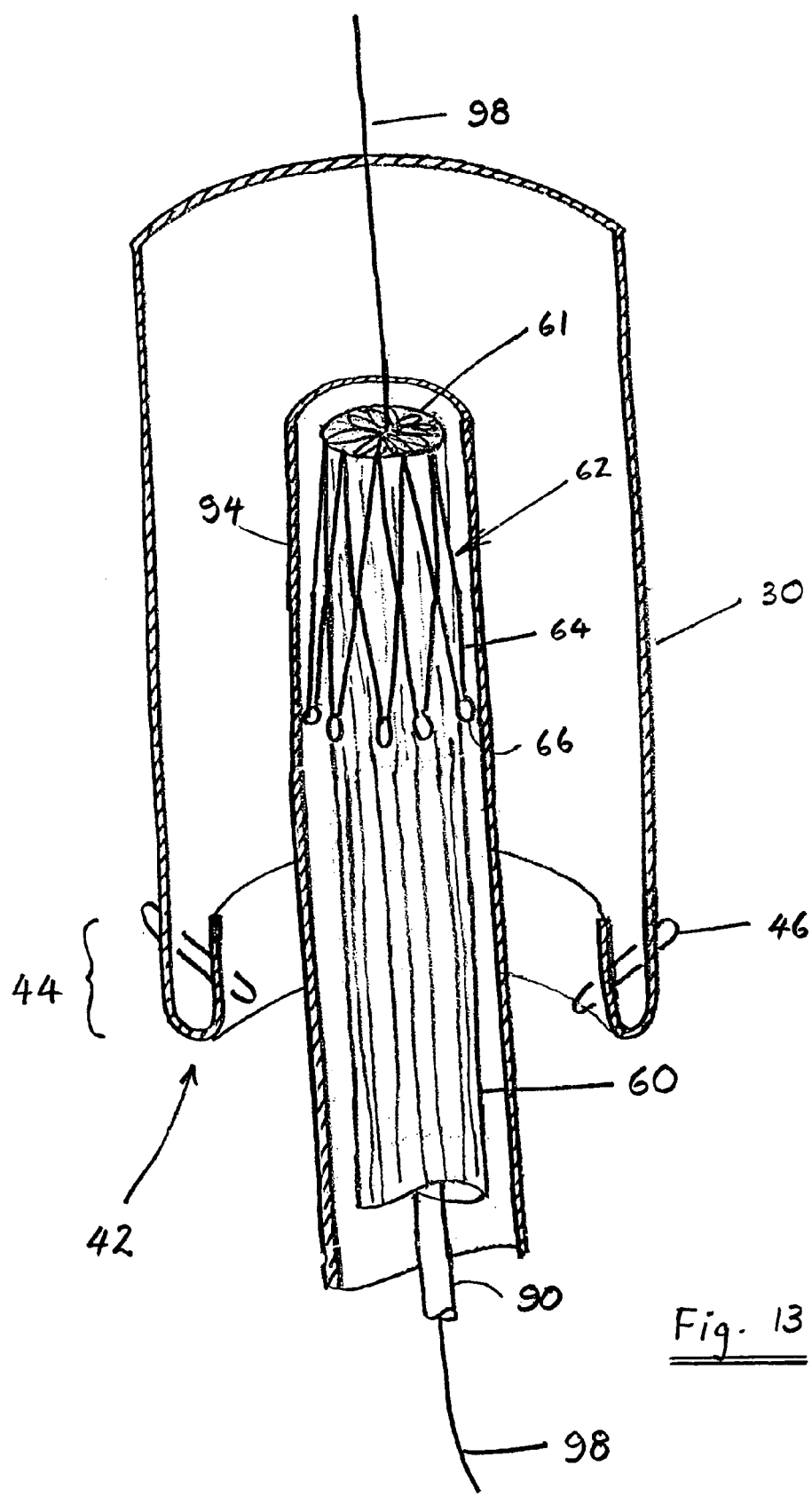
FIG. 13 is a partial cross-sectional view, depicting the delivery of a second element in relation to a first element.
Figure 14:
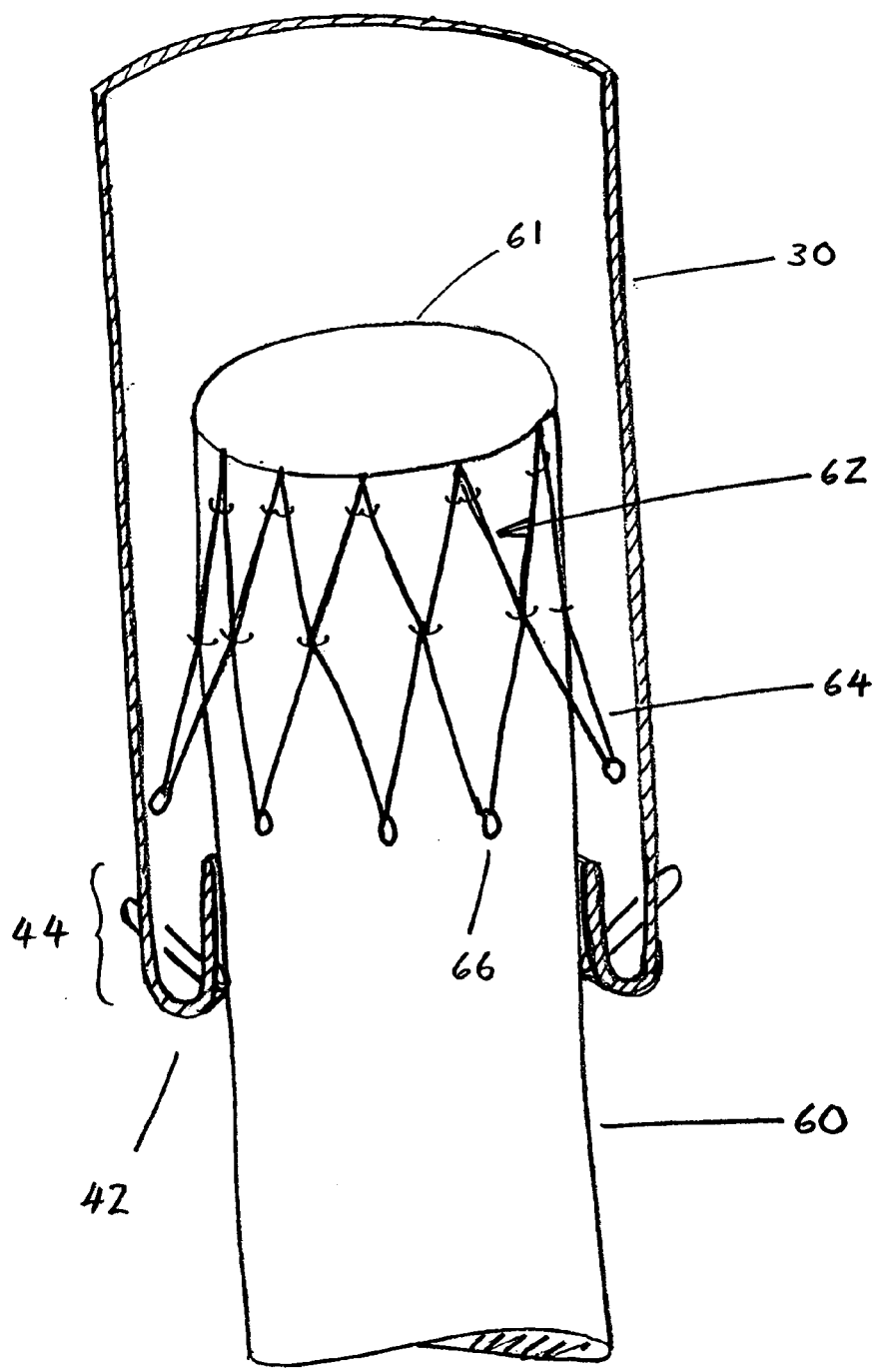
FIG. 14 is a partial cross-sectional view, depicting the second element of FIG. 3 in an expanded condition.
Figure 15:
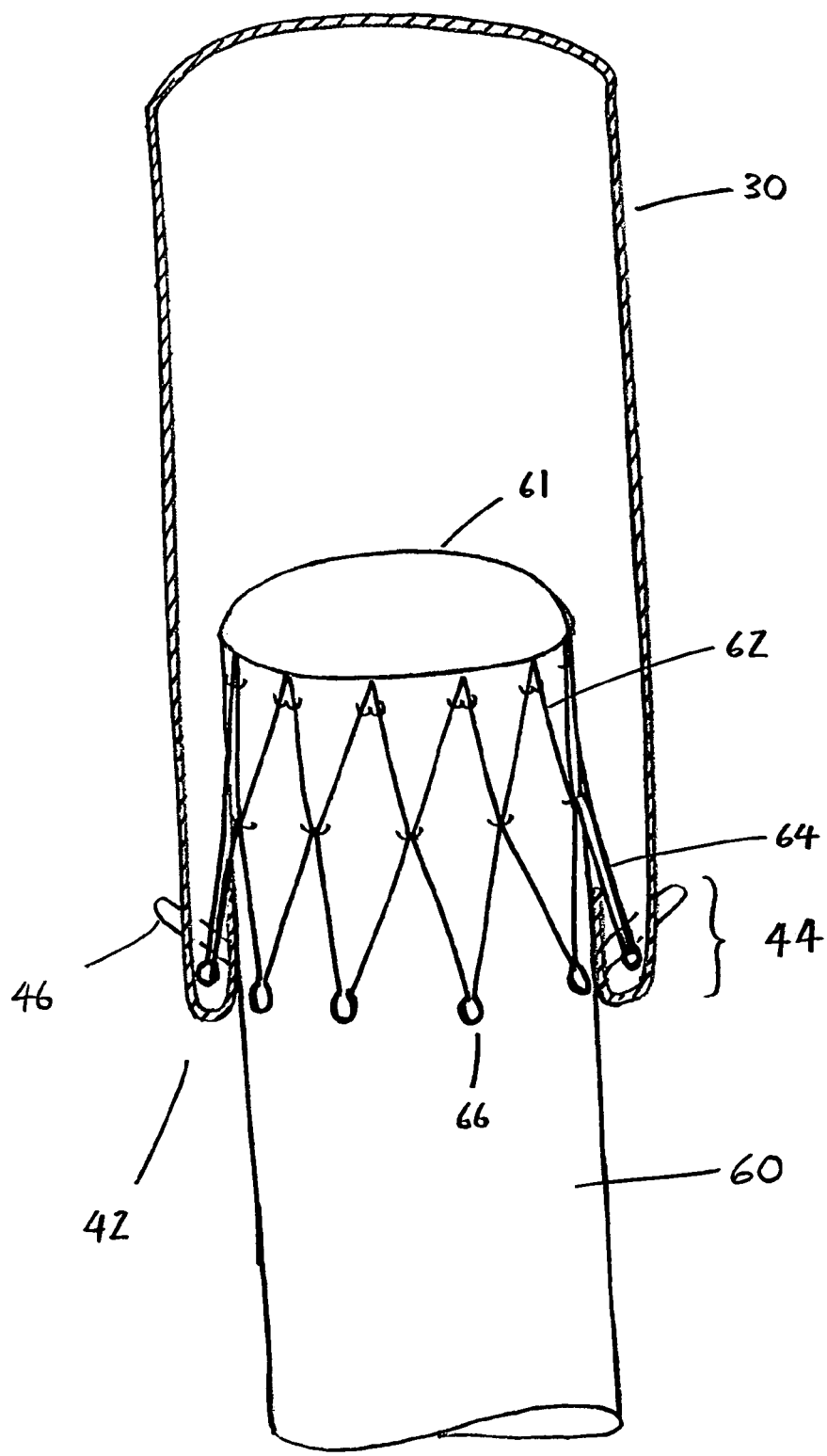
FIG. 15 is a partial cross-sectional view, depicting an engagement of the second element of FIG. 14 with the first element.

Turning now to FIGS. 13–15, a preferred method of joining first and second prosthetic elements of a modular endovascular prosthesis incorporating the present invention in the vasculature of a patient is described. FIGS. 13–15 depict the first prosthetic element with receiving element exemplified in FIG. 6 in combination with the second prosthetic element with receiving element exemplified in FIG. 8, but any suitable combination of receiving and protruding elements may be used according to the principles disclosed. A first prosthetic element 30 with receiving element 44 is initially deployed within the vascular system (not shown) of the patient. Methods of deploying flexible endovascular prosthetic elements within the vasculature of a patient are known in the art, in which deployment is conventionally achieved by placing the prosthetic element in a first compressed condition in a delivery sheath/capsule for insertion into the vascular system via delivery catheters. In general, once the first element 30 reaches the desired position within the vascular system, it is released from a delivery sheath/capsule, whereupon it is expanded from a compressed condition to an expanded condition, and may be attached to the wall of the vascular lumen using balloon-expanded or self-expanding attachment systems (not shown).

Once the first prosthetic element 30 has been deployed to assume its expanded condition, the superior end 61 of the second prosthetic element 60 configured with framework 62 in a compressed condition, is inserted into the lumen of the first prosthetic element 30 at the inferior end 42 thereof (FIG. 13). In the preferred method, the second prosthetic element 60 and framework 62 are disposed in a compressed condition over a delivery catheter 90 and confined within a jacket/sheath 94. The delivery catheter 90 with jacket 94 assembly may be inserted into the vascular system over a guidewire 98 configured to extend from the point of access (not shown) into the vasculature and through the interior of the first prosthetic element 30. When the entire framework 62 of the second element 60 is advanced beyond the receiving element of the first prosthetic element 30 (an annular pocket 44 in the case exemplified, but the principle applies to all embodiments of the receiving element), the second prosthetic element 60 and attached framework 62 are deployed by withdrawing the jacket 94, thereby permitting the framework 62 to assume an expanded condition (FIG. 14).

Accurate positioning of the second prosthetic element 60 relative to the first 30 may be achieved by using radiopaque markers, attached to the walls of both first and second prosthetic elements 30, 60, in conjunction fluoroscopy, for example. Use of radiopaque systems for positioning intraluminal devices is well known in the art and is not described here. It is to be further appreciated that additional expanding frameworks (not shown) may be used in conjunction with the first prosthetic element 30 in order to hold open the first element 30 at its inferior end 42, so that the superior end 61 of the second prosthetic element 60 may be introduced therein.

Once the second prosthetic element 60 with attached framework 62 is deployed and expanded (FIG. 14), the protruding struts 64 press against the interior wall of the first prosthetic element 30. The second prosthetic element 60 is then either moved longitudinally so that the protruding struts 64 of the framework 62 become seated in the receiving element 44 of the first prosthetic element 30, or it may be left in position and allowed to migrate thereto under the force of downstream fluid flow, so that it is eventually positioned with the protruding struts 64 seated in the receiving element 44 (FIG. 15). It is to be appreciated that, once the protruding struts 64 of the framework 62 are so seated, a robust mechanical barrier to distal migration of the second prosthetic element 60 relative to the first prosthetic element 30 is provided. Such a mechanical barrier has the advantage of being an effective barrier to axial separation of the first prosthetic element 30 from the second prosthetic element 60. Significantly, the overlap between the material of the first and the second prosthetic elements 30, 60 provides a fluid seal substantially preventing leakage of fluid through the junction to the region between the endovascular prosthesis and the vascular wall.

Figure 6:
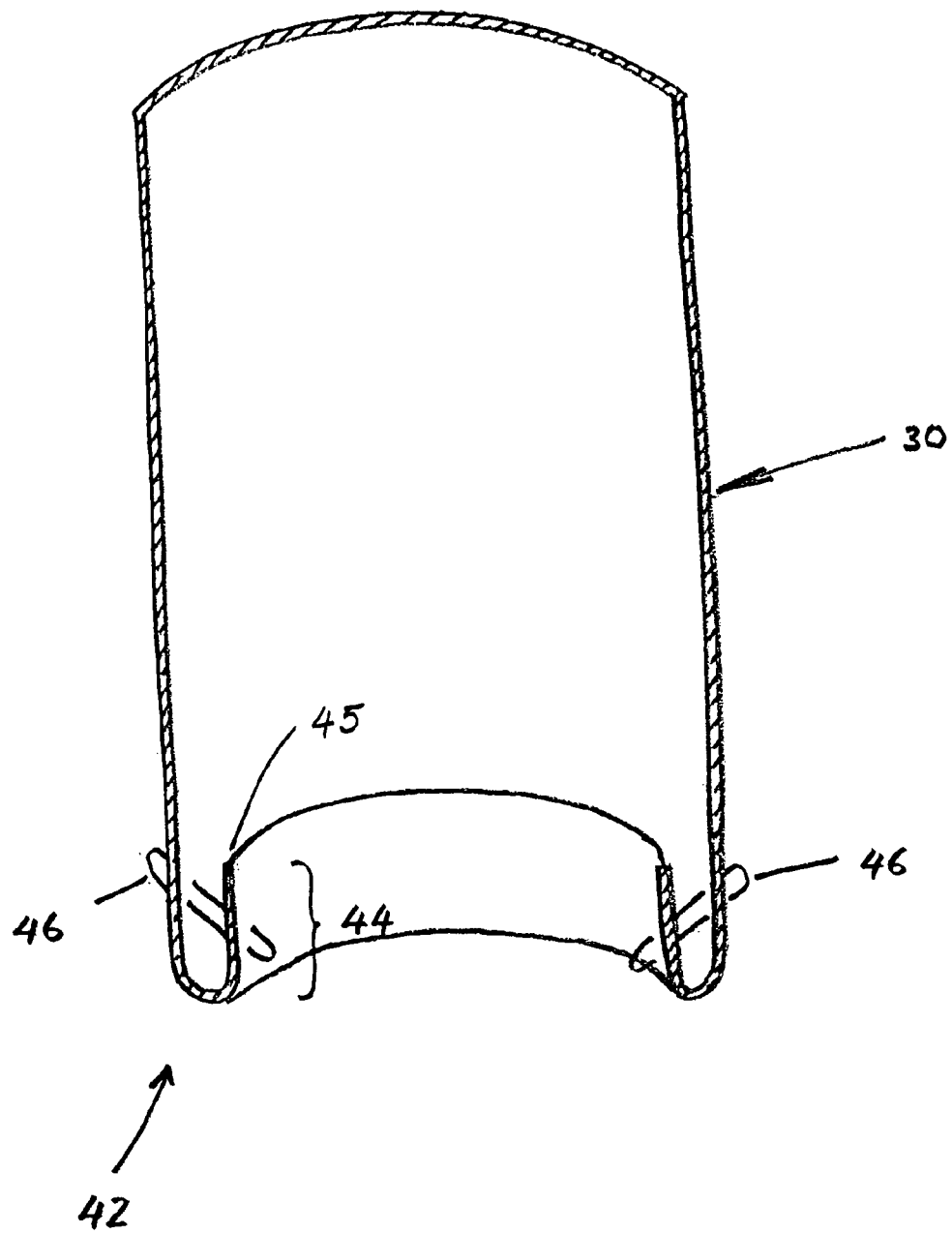
FIG. 6 is a cross-sectional view, depicting a second embodiment of a receiving element.
Figure 16:
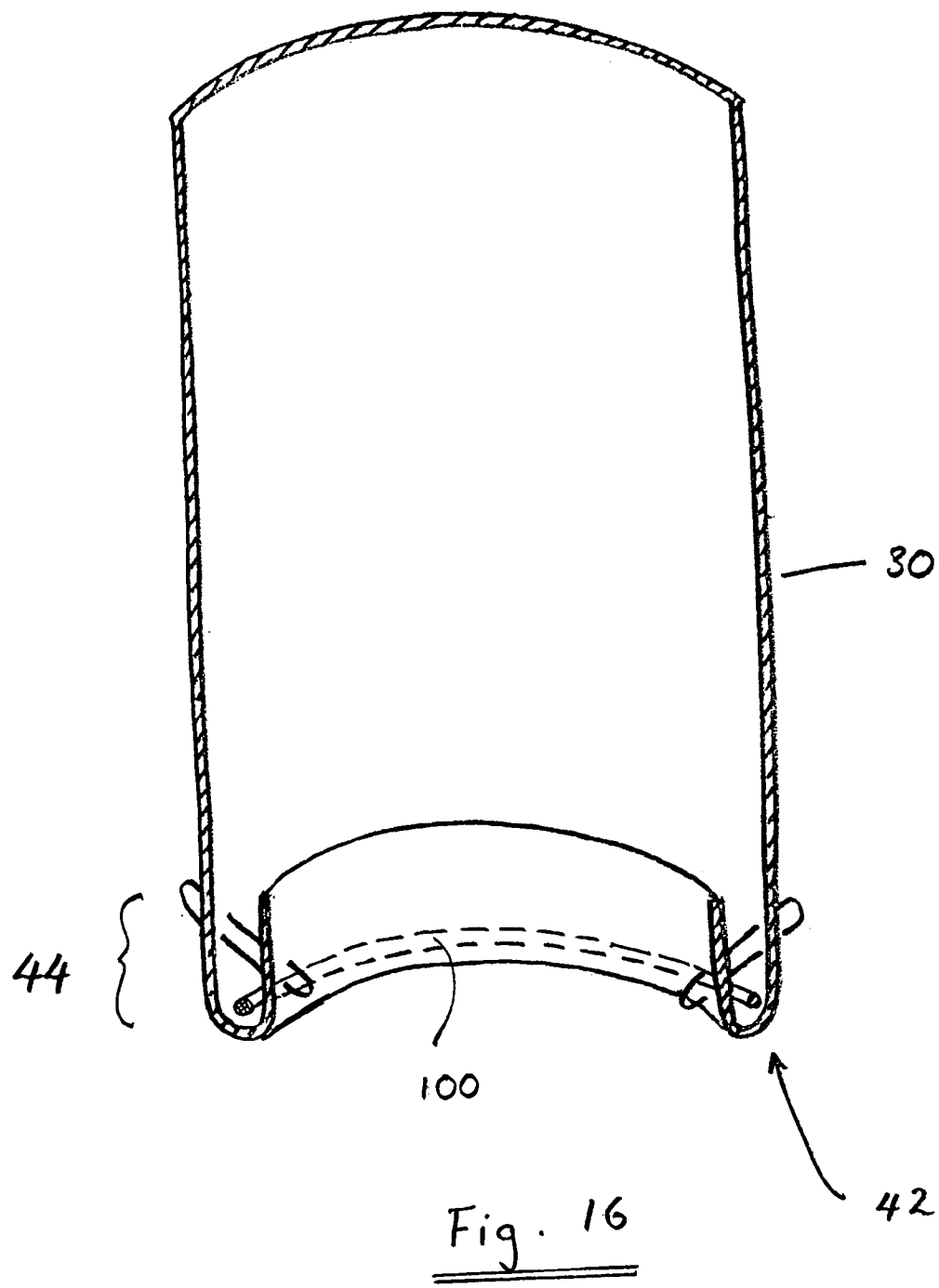
FIG. 16 is a cross-sectional view, depicting an expandable annular element incorporated into the embodiment shown in FIG. 6.

In a further aspect of the invention (FIG. 16), the receiving element 44 exemplified in FIG. 6 may be further equipped with an expandable annular element 100 that is inserted into the pocket 44. This arrangement facilitates holding the distal end 42 of the first prosthetic element 30 open, in order to aid the introduction of the second prosthetic element 60 therethrough. The annular element 100 is expandable between a first compressed condition and a second expanded condition. The annular element 100 may be compressed during delivery to expand upon deployment from a delivery catheter, and, like the self-expanding embodiment of the framework 62, may be made from a corrosion resistant material which has good spring and fatigue characteristics.

Figure 17:
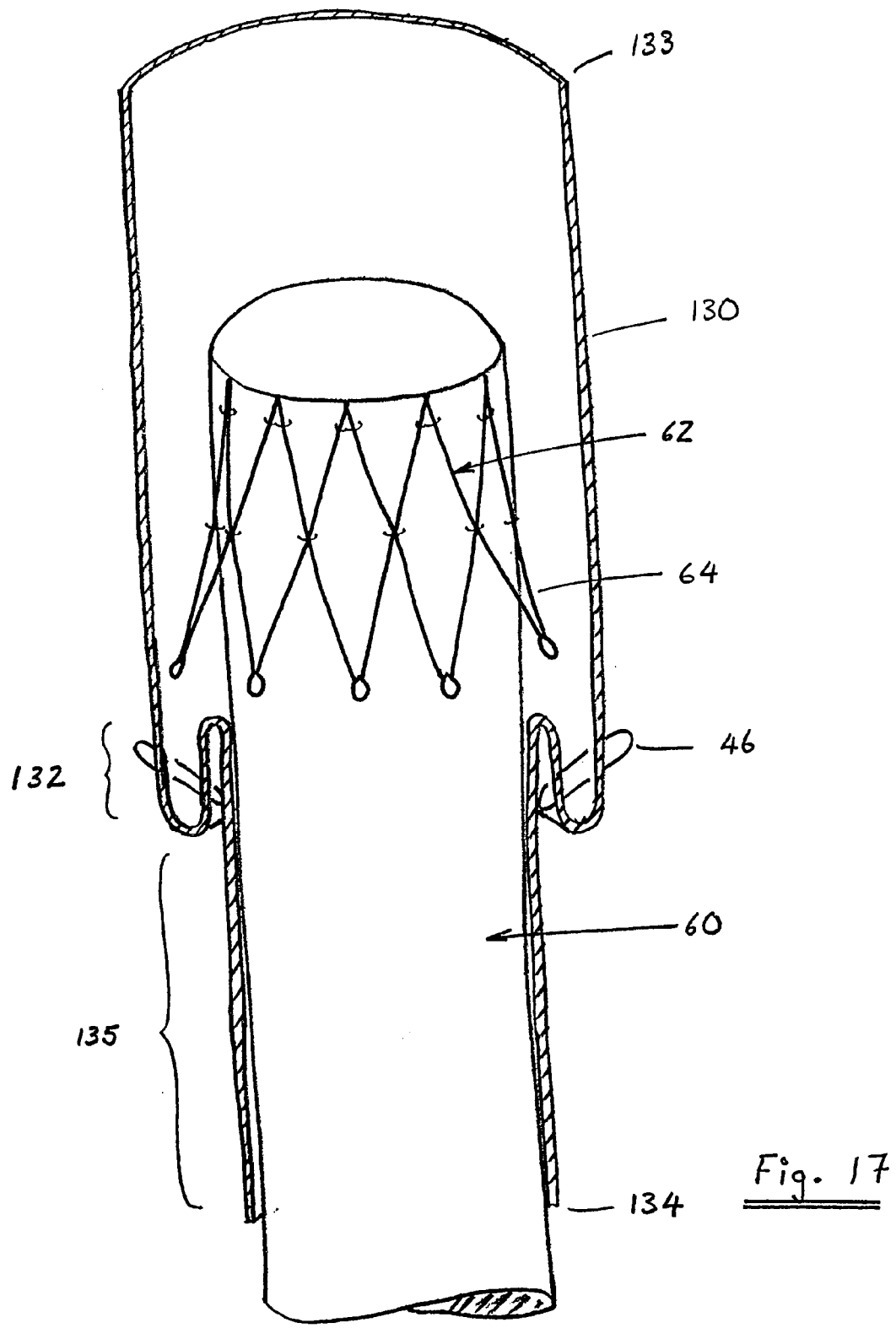
FIG. 17 is a partial cross-sectional view, depicting a fourth embodiment of the first element.
Figure 18:
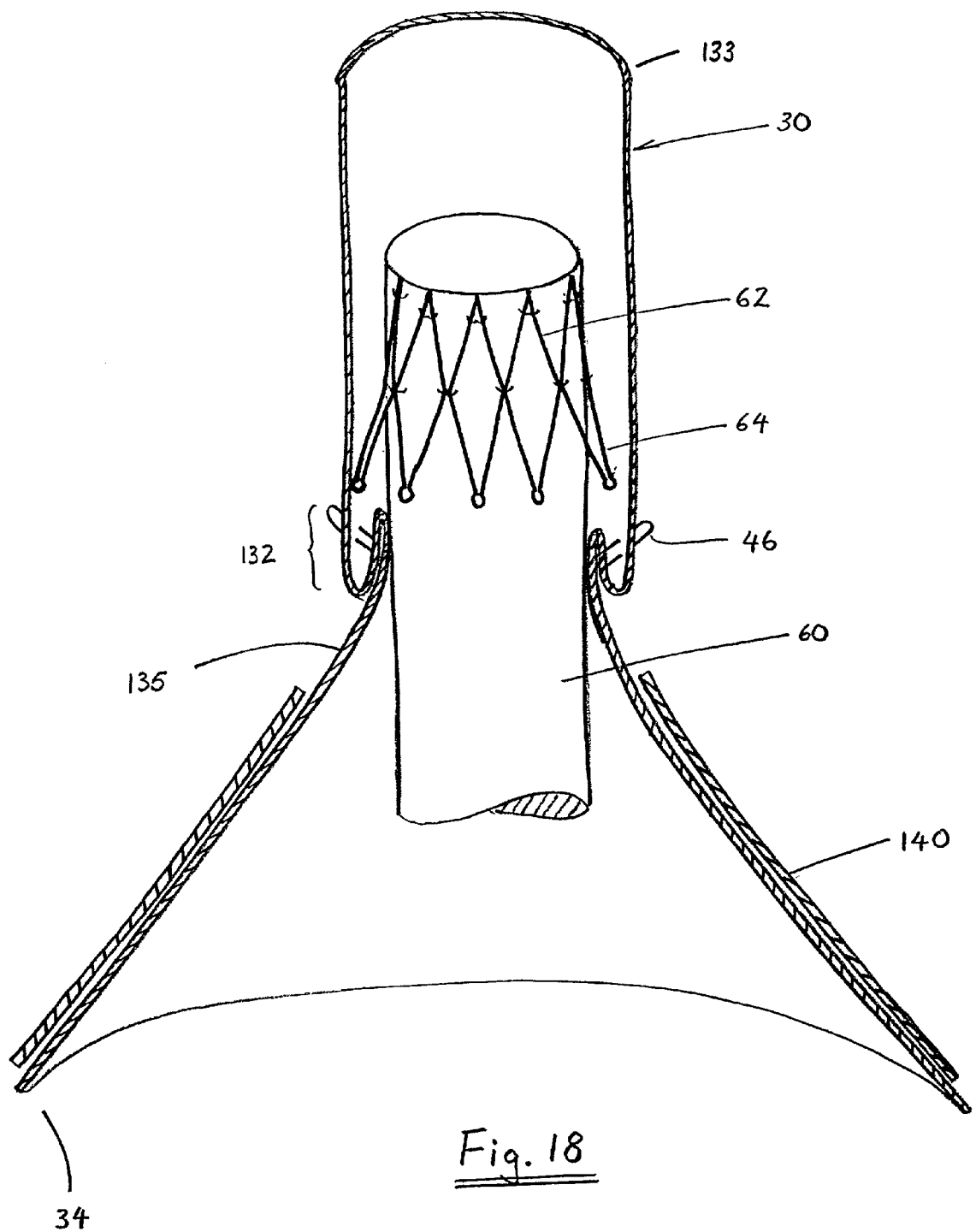
FIG. 18 is a partial cross-sectional view, depicting an alternative application of the present invention.

In yet a further aspect of the invention (FIG. 17), a first prosthetic element 130 includes an annular receiving element 132 formed in the internal walls of the first element 130 medial superior 133 and inferior 134 ends thereof. The receiving element 130 is formed by folding an annular section of the first element 130 upon itself and tacking the folds with connectors 46. This arrangement has the advantage of providing an added area of contact 135 between the material of the first and the second prosthetic elements 130, 60 which enhances the efficacy of the fluid seal between the elements. The first prosthetic element 130 may be held open at its inferior end by an expandable framework (not shown) of similar configuration to the expandable framework 62 described in the present invention. In a variation of this aspect, as exemplified in FIG. 18, the area of overlap 135 may be configured to have a bell-bottom profile, to facilitate guiding and inserting the second prosthetic element 60 into of the first prosthetic element 30. The bell-bottom profile may be held in position by an expandable framework 140, a similar arrangement which is shown in FIG. 1.

It will be apparent from the foregoing that, while particular forms of the invention have been illustrated and described, various modifications can be made without departing from the spirit and scope of the invention. Accordingly, it is not intended that the invention be limited, except as by the appended claims.

We claim:

1. A modular endovascular prosthesis, comprising:
    a first element having a cylindrical interior wall surface, an inferior end and a superior end and having a receiving element formed on the cylindrical interior wall surface of said first element, the receiving element having a receiving portion that suspends freely from the wall and can be translated both longitudinally or transversely with respect to the first element; and
    a second element having an inferior end and a superior end and further having at least one protrusion extending therefrom, said protrusion configured to be received within the receiving portion of said receiving element.

2. The prosthesis of claim 1, wherein said receiving element is defined by thread loops.

3. The prosthesis of claim 2, said receiving element further comprises connectors, said connectors attaching said thread loops to said first element.

4. The prosthesis of claim 2, wherein said thread loops engage said first element.

5. The prosthesis of claim 1, wherein said protruding element is an expandable framework having protruding struts.

6. The prosthesis of claim 5, wherein said second element comprises a wall defining a lumen having an inner and outer surface, and said expandable framework is configured on said inner surface.

7. The prosthesis of claim 5, wherein said expandable framework is self-expanding.

8. The prosthesis of claim 5, wherein said expandable framework is balloon-expanded.

9. A method for creating a junction between a first element and a second element of a modular endovascular prosthesis wherein both first and second elements define a lumen, comprising the steps:
    configuring the first element with a receiving element, the first element including a cylindrical interior wall surface and the receiving element having a receiving portion that suspends freely from the cylindrical interior wall surface of the first element and can be translated both longitudinally or transversely with respect to the first element;
    configuring the second element with a protruding element;
    deploying the first element;
    moving a portion of the second element into the lumen of the first element; and
    deploying the second element so that the protruding element is received within the receiving portion of the receiving element.

10. The method of claim 9, said step of deploying the first element further comprises permitting the first element to self-expand.

11. The method of claim 9, said step of deploying the second element further comprises permitting the second element to self-expand.

12. The method of claim 9, said step of configuring the first element with a receiving element further comprises:
    providing an expandable framework having protruding struts; and
    connecting the framework to the first element.

13. The method of claim 9, wherein said step of configuring the first element with a receiving element further comprises:
    providing a thread; and
    connecting the thread circumferentially to the first element.

* * * * *